(12) United States Patent
Blanc

(10) Patent No.: US 11,396,394 B2
(45) Date of Patent: Jul. 26, 2022

(54) METHOD AND DEVICE FOR ORIENTING AN UMBILICATED FRUIT, IN PARTICULAR FOR PACKAGING SAME

(71) Applicant: MAF AGROBOTIC, Montauban (FR)

(72) Inventor: Philippe Blanc, Montauban (FR)

(73) Assignee: MAF AGROBOTIC, Montauban (FR)

( * ) Notice: Subject to any disclaimer, the term of this patent is extended or adjusted under 35 U.S.C. 154(b) by 947 days.

(21) Appl. No.: 16/095,847

(22) PCT Filed: Apr. 24, 2017

(86) PCT No.: PCT/FR2017/050970
§ 371 (c)(1),
(2) Date: Oct. 23, 2018

(87) PCT Pub. No.: WO2017/187076
PCT Pub. Date: Nov. 2, 2017

(65) Prior Publication Data
US 2021/0276751 A1    Sep. 9, 2021

(30) Foreign Application Priority Data

Apr. 28, 2016 (FR) ...................... 16 53810

(51) Int. Cl.
*G01C 1/00* (2006.01)
*B65B 35/58* (2006.01)
*B65B 25/04* (2006.01)
*B65B 57/14* (2006.01)
*G01N 21/01* (2006.01)
*G01N 21/89* (2006.01)
(Continued)

(52) U.S. Cl.
CPC .............. *B65B 35/58* (2013.01); *B65B 25/04* (2013.01); *B65B 57/14* (2013.01); *G01N 21/01* (2013.01); *G01N 21/8901* (2013.01); *G01N 33/025* (2013.01); *G01N 21/251* (2013.01); *G01N 2021/0187* (2013.01); *G01N 2021/1765* (2013.01); *G01N 2021/845* (2013.01); *G01N 2021/8466* (2013.01)

(58) Field of Classification Search
CPC . G01C 1/08; G01C 21/20; G01C 3/22; G01C 15/00; A01K 97/00
USPC ........................................................ 356/144
See application file for complete search history.

(56) References Cited

U.S. PATENT DOCUMENTS

| 5,078,258 A | 1/1992 | van der Schoot |
| 5,626,238 A | 5/1997 | Blanc |

(Continued)

FOREIGN PATENT DOCUMENTS

EP    0 332 477    9/1989

OTHER PUBLICATIONS

International Search Report dated Jul. 12, 2017.

*Primary Examiner* — Md M Rahman
(74) *Attorney, Agent, or Firm* — IPSILON USA, LLP

(57) ABSTRACT

The invention relates to a method and device for orienting an umbilicated fruit, in which, during a first orientation phase (22), the presence of at least a portion of an umbilicus is detected in at least one initial image (II), then the fruit is driven (24) in spinning rotation about a first axis of rotation at an angular amplitude of between 5° and 45°, and then the presence of at least a portion of an umbilicus is detected in at least one subsequent image (IU). If at least a portion of an umbilicus is detected in at least one initial image (II) and no longer detected in each subsequent image (IU), the first orientation phase is stopped and the method is continued.

17 Claims, 12 Drawing Sheets

(51) Int. Cl.
    *G01N 33/02*     (2006.01)
    *G01N 21/25*     (2006.01)
    *G01N 21/84*     (2006.01)
    *G01N 21/17*     (2006.01)

(56) References Cited

U.S. PATENT DOCUMENTS

| | | |
|---|---|---|
| 5,737,901 A | 4/1998 | De Greef |
| 6,271,520 B1 | 8/2001 | Tao et al. |
| 6,691,854 B1 | 2/2004 | De Greef |
| 2014/0068418 A1 | 3/2014 | Yang |
| 2015/0259088 A1 | 9/2015 | Liedl |

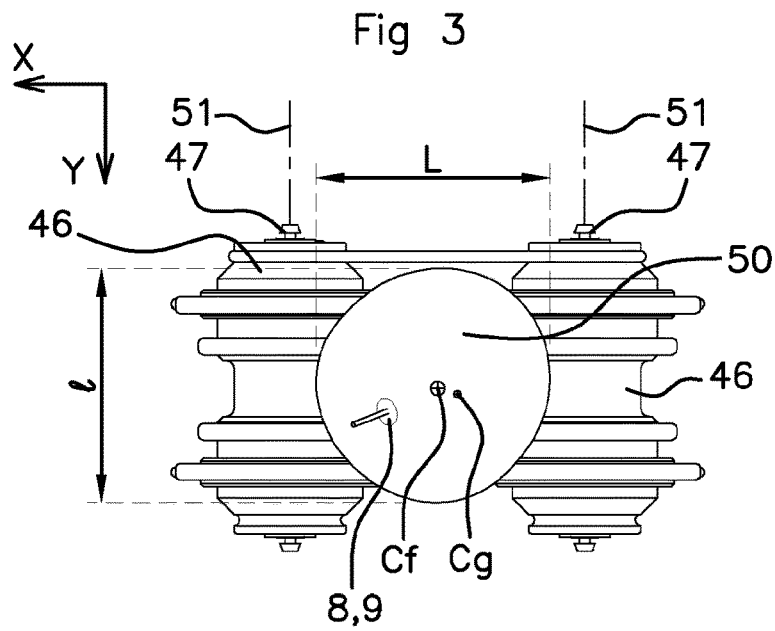
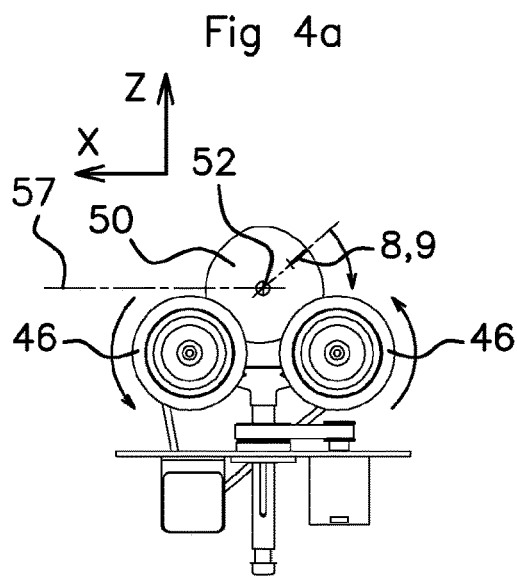
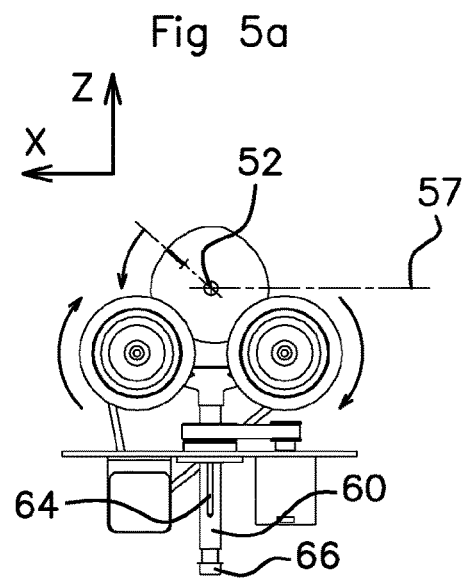
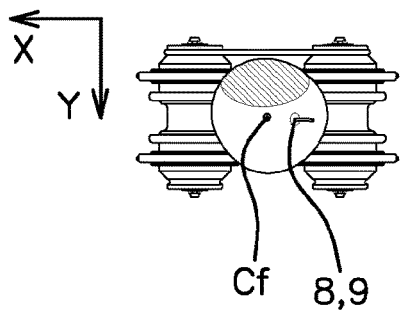
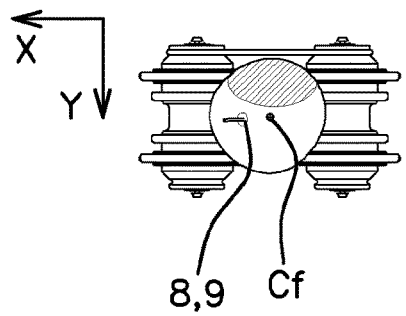

METHOD AND DEVICE FOR ORIENTING AN UMBILICATED FRUIT, IN PARTICULAR FOR PACKAGING SAME

RELATED APPLICATION

This application is a National Phase of PCT/FR2017/050970, filed on Apr. 24, 2017, which claims the benefit of priority from French Patent Application No. 16 53810, filed on Apr. 28, 2016, the entirety of which are incorporated by reference.

BACKGROUND

Field of the Invention

The invention relates to a method for orienting an umbilicated fruit. It particularly relates to a method for packaging umbilicated fruit comprising an orientation method according to the invention, to a computer program adapted to implement an orientation method according to the invention and/or a packaging method according to the invention, to a device for orienting an umbilicated fruit comprising a programmable processing unit programmed to implement an orientation method according to the invention and to a device for packaging umbilicated fruit comprising at least one fruit handling robot, said packaging device being adapted to implement a packaging method according to the invention.

Description of Related Art

Some fruit, named umbilicated fruit (apples, quinces, peaches, apricots, some tomatoes, some pears, etc.), comprises at least one umbilical depression on their periphery. This can involve, for example, a calyx basin in the vicinity of the calyx end of the fruit and/or a stalk cavity. When packaging such umbilicated fruit, it is often desirable to be able to control the spatial orientation of the fruit relative to the packaging, in order to promote its presentation to consumers. This is particularly the case when the fruit is packaged in crates or trays, particularly in cellular crates or trays, with each cell containing a fruit. Indeed, it is then preferable for all the fruit in the same packaging to be oriented with their stalk in the same direction and in the same way. It is also preferable for the fruit to be oriented for upwards presentation of surface portions where the colour is as appealing as possible and which are as uniform as possible for the same packaging.

Until now, despite the constant automation of modern packaging units, and the long-standing and constant research conducted in this field, the orientation of fruit is still performed manually by operators, with the tasks involved being particularly tedious and repetitive.

EP 332477 discloses a device for conveying fruit or vegetables comprising two longitudinal cylinders that are set into rotation and an advancement system disposed between the two cylinders comprising a plurality of rotary elements such as balls, translationally moving between the cylinders in order to push the objects parallel to the axes of the cylinders while the objects are set into rotation. Each ball is also actuated by a rotation movement on an axis perpendicular to the axis of rotation of the fruit that is imparted by the rotation of the cylinders until the ball is housed in one of the two natural cavities at the poles of the fruit. However, it has been found that this device is not effective enough, with many fruit ultimately not being correctly aligned.

EP 0727355 discloses a method for packaging fruit, such as apples and tomatoes, in which each fruit can be set into rotation by rollers about a first horizontal axis parallel to the axis of the rollers and about a second vertical axis with a view to orienting the fruit in a predetermined orientation. An optical analysis of each fruit is carried out and the generated images are compared with a reference image to determine whether the fruit has reached an acceptable orientation. Such a method, through comparison with a reference image, lacks reliability, with such a reference image in practice not providing a guarantee of the orientation of each fruit, given the significant variation in the shapes and dimensions of the fruit compared to the reference image. Thus, this method docs not necessarily tend towards an optimal orientation.

EP 1183197 discloses a method for orienting umbilicated fruit, such as apples or pears, allowing them to be oriented in the same direction and with the inflorescence oriented upwards in cellular packaging. Each fruit that is supported between two rollers can be set into spinning rotation about an axis parallel to the axis of the rollers, and can be lifted and set into spinning rotation about a vertical axis by virtue of a rotary lift support that is inserted between the rollers. This document does not disclose the method that can be implemented to detect the position of the inflorescence and to orient the inflorescence upwards, and assumes that this is always possible by rotation of the rollers. However, this clearly is not the case, to such an extent that this method suffers from such a lack of reliability that it cannot be practically implemented.

WO 2014/068418 discloses a method for orienting an umbilicated fruit in which the fruit is set into spinning rotation by rollers about a first axis X of rotation, whilst using a profilometer to capture images of the profile of the fruit in an orientation plane A comprising the first axis X, so as to detect a cusp in the profile and to measure the angle of incline of the main axis S of the fruit relative to this first axis X. The fruit is then set into rotation about a second axis Y of rotation perpendicular to the first axis X of rotation, so as to orient the main axis S of the fruit parallel to the first axis X of rotation in the orientation plane A.

This method also has several disadvantages. Firstly, detecting the profile requires a profilometer that is made up of a plurality of light sources and a plurality of cameras disposed around the fruit in a horizontal plane, which is particularly complex, requiring the placement of fragile and sensitive components above the rollers in the immediate vicinity of the fruit, with the risk of damaging its fragile components during steps of loading or unloading the rollers. Furthermore, the algorithms for analysing and detecting cusps in a profile are both particularly complex and insufficiently reliable. Indeed, detecting the main axis using a profile recognition algorithm through a comparison with a predetermined profile does not provide reliable results, with the predetermined profile not necessarily corresponding to that of all the objects that can be processed, and for which the profile is by nature extremely variable from one fruit to the next. It is also to be noted that the effectiveness of the detection of the main axis of the fruit and of its presence in a horizontal plane varies considerably as a function of the initial orientation of this main axis relative to the horizontal axis of rotation. Indeed, for example, if the main axis of the object is initially slightly inclined relative to the axis of rotation, the profile variations induced during the rotation are low. This results in, by geometrical construction, a significant margin of detection error of the main axis in the horizontal plane. This method also does not allow stalk-free fruit to be oriented.

Thus, despite a long-term perceived need and the various efforts undertaken previously, no previously proposed orientation method is reliable enough to be able to be practically used on an industrial scale, meaning that fruit is still manually oriented in packaging lines.

Therefore, the invention aims to overcome these disadvantages.

Objects and Summary

Thus, the invention aims to propose a method for orienting an umbilicated fruit with enhanced efficiency and reliability, in return for low manufacturing, installation and operating costs.

In particular, the aim of the invention is to propose such an orientation method that is reliable and effective enough, and is economical enough, to be competitive compared to manual fruit orientation operations.

It also aims to propose such an orientation method that is compatible with implementation in an agricultural environment, particularly in combination with a high output fruit packaging unit, particularly equipped with handling robots.

The invention also aims to propose such a method that allows the fruit to be oriented, on the one hand, with each umbilicus oriented in a predetermined direction and, on the other hand, with the most colourful part of each fruit oriented upwards.

It also aims to propose such a method that can be applied to any umbilicated, mono-umbilicated or bi-umbilicated fruit, with or without a stalk.

Throughout the document, the term "at least substantially" indicates, as is common practice, that a structural feature, such as a value, or a functional feature, must not be seen as an abrupt discontinuity, which would have no physical meaning, but not only covers this structure or this function, but also slight variations in this structure or this function, which produce, within the considered technical context, an effect of the same type, or otherwise of the same degree. Furthermore, the term "parallel" is used throughout the document as encompassing the case of coincident straight lines or coincident planes.

Therefore, the invention relates to a method for orienting an umbilicated fruit, wherein:
 during a first orientation phase the fruit is supported and set into spinning rotation about a first axis of rotation;
 during a second subsequent orientation phase the fruit is supported and set into spinning rotation about a second axis of rotation orthogonal to the first axis of rotation;
 an optical analysis of an upper surface of the fruit is carried out at least during at least part of the first orientation phase using at least one camera disposed above the fruit capturing images of said upper surface of the fruit, said images being transmitted to an image processing unit adapted to analyse said images and to produce optical analysis results depending on the orientation of the fruit;
 the rotation of the fruit about each of the two axes of rotation is controlled at least as a function of said optical analysis results of the fruit; characterised in that;
 the first orientation phase comprises the following steps:
  an initial optical analysis step, during which.
   at least one image, named initial image, of the fruit is captured on an optical image capturing axis not parallel to the first axis of rotation;
   each initial image is analysed by optical analysis, with the presence of at least one portion of an umbilicus being detected in each initial image;
  then a rotation step, during which the fruit is set into spinning rotation about the first axis of rotation at an angular amplitude between 5° and 45°;
  then a subsequent optical analysis step, during which;
   at least one image, named subsequent image, of the fruit is captured on the same optical image capturing axis as the initial image;
   each subsequent image is analysed by optical analysis, with the presence of at least one portion of an umbilicus being detected in each subsequent image;
  the processing unit executes a step of conditional decision-making, according to which, if a first condition is met by the optical analysis results of each initial image and of each subsequent image, the first orientation phase is stopped and the method is continued, said first condition being met if at least one portion of an umbilicus is detected in at least one initial image and is no longer detected in each subsequent image.

Following numerous unsuccessful tests, it has been found that combining the features of a method according to the invention surprisingly allows near perfect reliability to be obtained for the orientation of the fruit, and that this is equally the case for apples, pears, tomatoes, etc. Indeed, capturing at least two successive images, separated by a rotation of the fruit about the first axis of rotation and the step of conditional decision-making, particularly allow each umbilicus of the fruit to be oriented in a predetermined plane, named first orientation plane, containing the first axis of rotation and not parallel, particularly at least substantially perpendicular, to the optical image capturing axis of the camera capturing the initial and subsequent images.

A method according to the invention can be the subject of various variations with respect to the steps executed after the first orientation phase, if said first condition is met (subsequent steps can be provided, particularly for orienting each umbilicus in a favoured direction of said first orientation plane and/or for orienting a more colourful portion of the fruit upwards and/or for orienting the stalk of the fruit in a predetermined direction), and with respect to the steps executed after the step of conditional decision-making, if said first condition is not met (with a view to optimising the orientation of each umbilicus of the fruit in said plane perpendicular to the optical image capturing axis). For example, other optical analysis devices can be provided for performing optical analyses at other image capturing angles. This being the case, an advantage of the invention is that, in some embodiments, it allows precise and definitive orientation of the fruit without adding an additional optical analysts device, and does so in a simple, reliable and effective manner.

Thus, in some advantageous embodiments of an orientation method according to the invention, if said first condition is not met, the steps of rotation and of subsequent optical analysis of the first orientation phase are repeated, then the step of conditional decision-making is repeated by the processing unit by considering the subsequent image captured before repeating the steps of rotation and of subsequent optical analysis, as an initial image.

More specifically, advantageously and according to the invention, according to the step of conditional decision-making:
 if at least one portion of an umbilicus is detected in at least one initial image and in at least one subsequent image, the steps of rotation and of subsequent optical analysis of the first orientation phase are repeated;

if at least one portion of an umbilicus is not detected either in each initial image or in each subsequent image, the steps of rotation and of subsequent optical analysis of the first orientation phase are repeated, as long as the total angular amplitude of the rotation of the fruit resulting from the various steps of rotation carried out during the first orientation phase is below a predetermined angular amplitude, named maximum rotation amplitude, between 180° and 360°, particularly of the order of 270°;

if at least one portion of an umbilicus is not detected either in each initial image or in each subsequent image, the steps of rotation and of subsequent optical analysis of the first orientation phase are repeated, and if the total angular amplitude of the rotation of the fruit resulting from the various steps of rotation previously carried out during the first orientation phase is greater than or equal to said maximum rotation amplitude, the first orientation phase is stopped and the method is continued;

if at least one portion of an umbilicus is not detected in each initial image but is detected in at least one subsequent image, the steps of rotation and of subsequent optical analysis of the first orientation phase are repeated, then the step of conditional decision-making is repeated by the processing unit by considering the subsequent image captured before repeating the steps of rotation and of subsequent optical analysis, as an initial image.

Such an orientation method according to the invention ensures rapid convergence of the orientation of each umbilicus of the fruit in a first orientation plane that is at least substantially perpendicular to the optical image capturing axis of each initial image and of each subsequent image captured during said first orientation phase, particularly in a first orientation plane that is at least substantially, particularly strictly, horizontal.

Said optical image capturing axis must not be parallel to the first axis of rotation, so that each subsequent image is an image of an upper surface portion of the fruit distinct from that viewed by each initial image. Said image capturing axis can be inclined relative to the first axis of rotation. However, preferably, said optical image capturing axis is at least substantially, particularly strictly, orthogonal, preferably at least substantially, particularly strictly; perpendicular to the first axis of rotation. However, it is to be noted that there is nothing to prevent, in some variations, the provision of a plurality of cameras for forming a plurality of initial images (or a plurality of subsequent images), in different wavelength spectra or in tire same wavelength spectra, said cameras being oriented on image capturing axes that are at least substantially parallel but remote from each other, for example, passing cither side of the first axis of rotation. There is also nothing to prevent an initial image (or a subsequent image) from being captured by combining a plurality of images captured by a plurality of cameras, for example, by forming, through computation, an average of a plurality of original images captured on optical image capturing axes that are at least substantially parallel (said optical image capturing axis of the initial image or of the subsequent image then being a virtual optical axis parallel to the optical image capturing axes of the original images and being located between the latter, at the same distance therefrom, particularly in the intermediary position).

Furthermore, with the first axis of rotation being an axis of spinning rotation of the fruit, it is an axis that passes through the fruit, preferably at least substantially through a geometrical centre or a centre of gravity of the fruit. However, it is to be noted that this first axis of rotation can only be approximately defined relative to the fruit, according to the shape and the dimensions of the outer surface of the fruit, when said fruit is set into spinning rotation by rollers supporting the fruit. Similarly, the second axis of rotation, being an axis of spinning rotation of the fruit, is an axis that passes through the fruit, preferably at least substantially through a geometrical centre or a centre of gravity of the fruit. Consequently, these two axes of rotation preferably at least substantially intersect at a point passing through the fruit, preferably at least substantially at a geometrical centre or a centre of gravity of the fruit. Thus, the two axes of spinning rotation of the fruit are not only orthogonal to each other, but also at least substantially perpendicular to each other.

In some embodiments, advantageously and according to the invention, the second axis of rotation is perpendicular to a plane, named first orientation plane, containing the first axis of rotation and not parallel to the optical image capturing axis. In the preferred embodiments, in which the optical image capturing axis is at least substantially, particularly strictly, orthogonal to the first axis of rotation, advantageously and according to the invention, the second axis of rotation is at least substantially, particularly strictly, parallel to said optical image capturing axis. In the preferred embodiments, in which the optical image capturing axis is at least substantially, particularly strictly, perpendicular to the first axis of rotation, advantageously and according to the invention, the second axis of rotation is at least substantially, particularly strictly, coincident with said optical image capturing axis.

Furthermore, in some preferred embodiments, the first axis of rotation is contained in a horizontal plane and the second axis of rotation is vertical. Furthermore, preferably, said optical image capturing axis is then also vertical.

Moreover, the rotation step of the first orientation phase of a method according to the invention can be the subject of diverse variations, particularly for minimising the duration of this rotation step and of the entire method according to the invention, and this is particularly as a function of the geometrical and dimensional features of the fruit.

Thus, in particular, during this rotation step, the fruit is set into rotation at an angular amplitude between 10° and 20°, in particular of the order of 15° for apples, with this angular amplitude value particularly depending on the optical analysis technique used to detect an umbilicus in the images and the average relative dimensions of the umbilical depression of each umbilicus of the fruit. The optimal value can be determined experimentally. In particular, it must be low enough to ensure that the fruit is effectively moved (without slippage) and to obtain sufficient accuracy of movement, so that the umbilicus is correctly oriented after the rotation, if only one portion of this umbilicus is detected in the initial image. It is large enough to optimise the duration of this step and of the entire method.

Similarly, in some advantageous embodiments, said step of initial optical analysis comprises the detection of a centre of the fruit in at least one initial image, and, if at least one portion of an umbilicus is detected in at least one initial image, during the subsequent rotation step the fruit is set into rotation in a direction that is determined by the respective detected positions of the centre of the fruit and of the umbilicus, and is selected to minimise the angular movement amplitude of the umbilicus towards a plane, named first orientation plane, containing the first axis of rotation and not parallel to the optical image capturing axis. In the aforementioned preferred embodiments, said first orientation plane is a plane that is at least substantially, particularly strictly, perpendicular to said optical image capturing axis and contains the first axis of rotation.

Any suitable imaging technique can be used to detect an umbilicus in a fruit during an optical analysis step of a method according to the invention. This being the case, it has been noted that surprisingly reliable results have been obtained by analysing infrared imaging grey scales. Thus, advantageously and according to the invention, during each optical analysis step, at least one image, named infrared image, is captured using at least one infrared camera, and the presence of at least one portion of an umbilicus [is detected] in each infrared image in the form of a spot having a grey scale that is higher than a predetermined grey scale and is smaller than that of the frail, but is larger than a predetermined dimension. This spot can be detected in the infrared image using any suitable image analysis technique, particularly using an algorithm comprising a convolution and a convolution kernel. This is particularly the case for each optical analysis step of the first orientation phase of a method according to the invention. Indeed, it has been found that an umbilicus of a fruit is represented by a darker spot in infrared imaging.

Advantageously and according to the invention, the fruit is illuminated by an infrared light source, the wavelength of which is greater than 500 nm and lower than 1,100 nm, for example, of the order of 740 nm, and at least one infrared camera is used that allows the wavelengths to be detected in the vicinity of that of the infrared light source, for example, an infrared camera that is sensitive between 350 nm and 1,100 nm with a high-pass filter having a cut-off wavelength that is slightly below that of the infrared light source, for example, of the order of 700 nm.

As previously mentioned, the steps executed after the first orientation phase of a method according to the invention can be the subject of several variations. In some preferred embodiments, advantageously and according to the invention, at the end of the first orientation phase the processing unit:
  identifies the last captured image, in which at least one portion of an umbilicus is detected by optical analysis, determines the position of a centre of the fruit in this last image, and computes the value of an angle, named azimuth, formed between the first axis of rotation and an axis, named umbilical axis, passing through the umbilicus and the centre of the detected fruit;
  then commands a rotation of the fruit about the second axis of rotation during the second orientation phase at an angular amplitude that is determined by the computed azimuth value, so as to orient the umbilical axis at a predetermined orientation relative to the first axis of rotation, in particular either at least substantially parallel to the first axis of rotation, particularly strictly parallel to the first axis of rotation, or at least substantially orthogonal to the first axis of rotation, particularly strictly orthogonal to the first axis of rotation.

Furthermore, an orientation method according to the invention also advantageously comprises a colorimetric optimisation step allowing the most colourful portions of the fruit to be placed in the same predetermined position. Thus, advantageously, a method according to the invention comprises, after the second orientation phase, a subsequent orientation phase, during which:
  the fruit is supported mid set into rotation over an angular rotation amplitude of at least 360° about the first axis of rotation;
  an optical analysis of an upper surface of the fruit is carried out to detect a portion of said upper surface, named most colourful portion, having a maximum amount of colour;
  the rotation of the fruit is interrupted so as to place said most colourful portion on top.

In some variations of a method according to the invention there is nothing to prevent the provision of steps different from the aforementioned steps and/or the intermediate steps between the aforementioned steps. For example, at least one step of dimensional morphological analysis can be provided prior to rotation on the second axis of rotation and/or at least one step of seeking a morphological error can be provided before or after the colorimetric optimisation step.

The invention is applicable to the orientation of fruit comprising a single umbilicus or a plurality of umbilici (fruit named bi-umbilicated fruit), namely a calyx basin and a stalk cavity, with or without a stalk.

However, the invention more specifically relates to a method for orienting a stalked fruit, characterised in that it comprises, after the second orientation phase, a step of morphological optical analysis adapted to allow the detection of the position of a stalk of the fruit. Such a step of morphological optical analysis allows the position of the stalk to be distinguished relative to that of the calyx basin. It can be executed, for example, in the case of apples, on the basis of captured images and by detecting the position of the largest diameter of the fruit relative to a diameter of the fruit passing through the centre of the fruit perpendicular to the umbilical axis of the fruit, with the stalk being located on the largest diameter side of the fruit.

The position of the stalk of the fruit that is thus detected can be simply stored and subsequently taken into account, for example, by a handling robot in order to correctly orient the fruit in a cellular package. This being the case, in some embodiments, the method according to the invention further comprises, after the step of morphological optical analysis, a subsequent step of rotation, during which the fruit is set into rotation about the second axis of rotation at a determined angular amplitude for placing the stalk in a predetermined angular position relative to the first axis of rotation.

The invention also relates to an orientation device adapted to implement an orientation method according to the invention. Therefore, the invention also relates to a device for orienting an umbilicated fruit comprising:
  a first fruit support adapted to support a fruit and to set it into spinning rotation about a first axis of rotation;
  a second fruit support adapted to support a fruit and to set it into spinning rotation about a second axis of rotation orthogonal to the first axis of rotation;
  a device for optically analysing an upper surface of the fruit, comprising at least one camera disposed above the fruit in order to be able to capture images of said upper surface of the fruit;
  a programmable processing unit adapted to:
    analyse the images and to produce optical analysis results dependent on the orientation of the fruit;
    control the rotation of the fruit about each of the two axes of rotation at least as a function of said optical analysis results of the fruit:
characterised in that said programmable processing unit is programmed to implement an orientation method according to the invention.

The invention also particularly relates to a method for packaging umbilicated fruit in cellular packages, in which each fruit is placed in a packaging cell at a predetermined orientation, characterised in that it comprises a method for orienting each fruit according to the invention.

The invention also relates to a packaging device for implementing a packaging method according to the invention. Therefore, it also relates to a device for packaging umbilicated fruit comprising devices for orienting fruit and at least one fruit handling robot that is adapted to place each fruit in a cell of a cellular package at a predetermined orientation, characterised in that it comprises at least one orientation device according to the invention.

The programmable processing unit described in the present document can be fully or partly formed by a programmable computer system able to be implemented by one computer program or by a plurality of computer programs, which can exist in various forms, both active and inactive, in a single computer system or in a plurality of computer systems. For example, they can consist of software programs formed by program instructions in source code, object code, executable code or in another format for executing at least part of the steps of a method according to the invention. They can be in the form of a downloadable data stream or a computer readable medium, which includes recording and signal devices, in compressed or uncompressed format.

Thus, the invention relates to a computer program comprising computer program code instructions, particularly computer program code instructions forming a downloadable data stream and/or instructions recorded on a medium that can be used in a programmable processing unit, characterised in that it comprises programming means that etui be read by a programmable processing unit and that are adapted to, once executed by said programmable processing unit, execute an orientation method according to the invention and/or a packaging method according to the invention with said programmable processing unit and with a device for orienting each fruit that is adapted to support and to set each fruit into spinning rotation about said first axis of rotation and about said second axis of rotation, particularly with an orientation device according to the invention.

The invention also relates to a computer program comprising computer program code instructions, particularly computer program code instructions forming a downloadable data stream and/or instructions recorded on a medium that can be used in a programmable computer and/or robotics system, characterised in that it comprises programming means that can be read by a programmable computer and/or robotics system and that are adapted to, once executed by a programmable processing unit of said programmable computer and/or robotics system (particularly loaded in the memory of this programmable processing unit), execute an orientation method according to the invention and/or a packaging method according to the invention with said programmable processing unit and with a device for orienting each fruit that is adapted to support and to set each fruit into spinning rotation about said first axis of rotation and about said second axis of rotation.

The invention also relates to a computer program product comprising computer program code instructions, characterised in that it comprises programming means that can be read by a programmable processing unit of a computer and/or robotics system, said programming means being adapted to, once executed by said programmable processing unit, execute an orientation method according to the invention and/or a packaging method according to the invention with said programmable processing unit and with a device for orienting each fruit that is adapted to support and to set each fruit into spinning rotation about said first axis of rotation and about said second axis of rotation, particularly with an orientation device according to the invention.

The invention also relates to a medium that can be used in a programmable computer and/or robotics system, said medium comprising computer program code instructions that are recorded on said medium and that can be used in a programmable processing unit of such a programmable computer and/or robotics system, characterised in that it comprises, recorded on this medium, programming means that can be read by a programmable processing unit of a computer and/or robotics system, said programming means being adapted to, once executed by said programmable processing unit execute an orientation method according to the invention and/or a packaging method according to the invention with said programmable processing unit and with a device for orienting each fruit that is adapted to support and to set each fruit into spinning rotation about said first axis of rotation and about said second axis of rotation, particularly with an orientation device according to the invention.

As used throughout the present document, the term "medium that can be used in a programmable computer and/or robotics system" can refer to any device that can contain, store, communicate, propagate or carry a program so that it can be used by, or in connection with, such a programmable computer and/or robotics system, a terminal, an apparatus, or a device for executing program code instructions. Such a medium that can be used in a programmable computer and/or robotics system can be, by way of a non-limiting example, a terminal, a device, an apparatus, a system or an electronic, magnetic, optic, electromagnetic, infrared or semi-conductor propagation medium. Some specific non-exhaustive examples of such a medium can be as follows: a computer terminal, an electrical connection with one or more conductors, a bulk memory (hard drive, USB stick, etc.), a disc, a random-access memory (RAM), a read-only memory (ROM), an erasable programmable read-only memory (EPROM or flash memory); an optical fibre, an optical reading memory (read-only or rewritable compact disc). The invention also relates to a downloadable data stream representing a computer program according to the invention.

The invention also relates to an orientation method, an orientation device, a packaging method, a packaging device, a computer program, a computer program product, a medium that can be used in a programmable computer and/or robotics system, characterised, in combination, by all or part of the features mentioned previously or hereafter.

Further aims, features and advantages of the invention will become apparent upon reading the following description, which is provided by way of a non-limiting example, and with reference to the accompanying drawings, in which:

BRIEF DESCRIPTION OF THE DRAWINGS

FIG. 3 is a schematic top view showing the geometrical features of a fruit as viewed by an optical analysis device of an orientation device according to one embodiment of the invention;

FIGS. 4a and 4b are schematic elevation and top views, respectively, of a fruit support of an orientation device showing a first example of a rotation step of a first orientation phase of an orientation method according to one embodiment of the invention;

FIGS. 5a and 5b are schematic elevation and top views, respectively, of a fruit support of an orientation device showing a second example of a rotation step of a first orientation phase of an orientation method according to one embodiment of the invention;

An umbilicated fruit, such as an apple, has at least one umbilicus determining an axis, named umbilical axis 10 (FIG. 16), relative to which the fruit is generally at least substantially rotationally symmetrical. An umbilicated fruit can have a single umbilicus generally corresponding to a stalk cavity (peaches, apricots, etc.) or, rather, as is the case for apples, can have two opposite umbilici 8, 9, one 8 of which corresponds to a stalk cavity, the other one 9 of which corresponds to a calyx basin, with the umbilical axis 10 passing through the two opposite umbilici 8, 9. A method according to the invention for orienting an umbilicated fruit has the following main steps.

Figure 17:
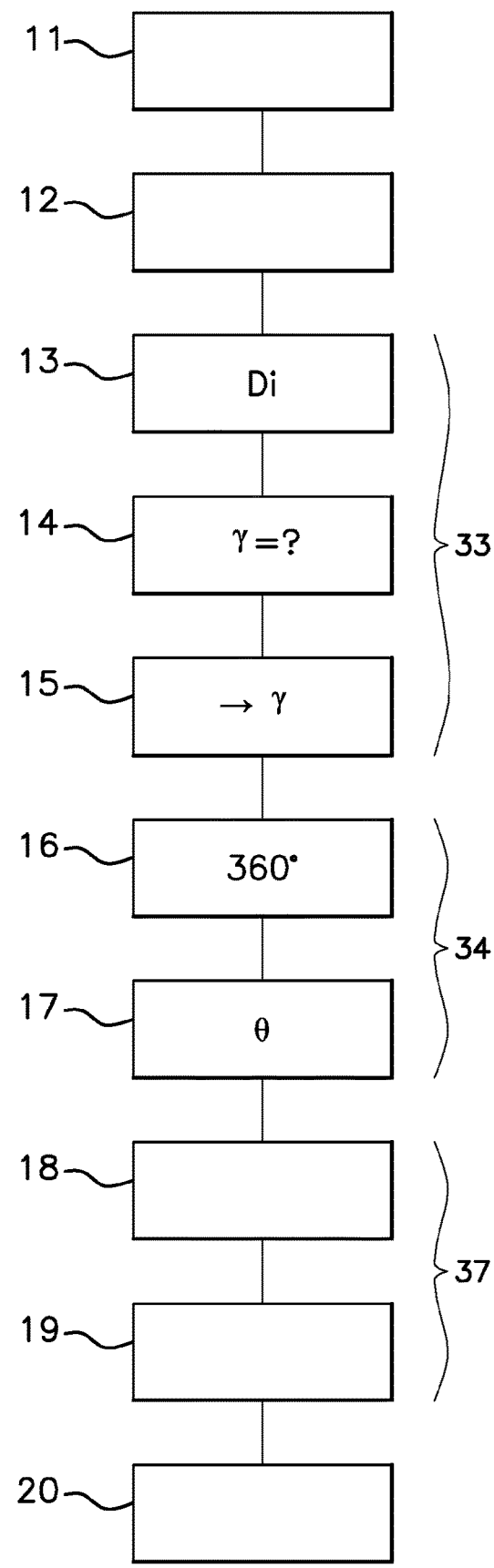
FIG. 17 is a flow chart of a packaging method according to one embodiment of the invention.
Figure 18:
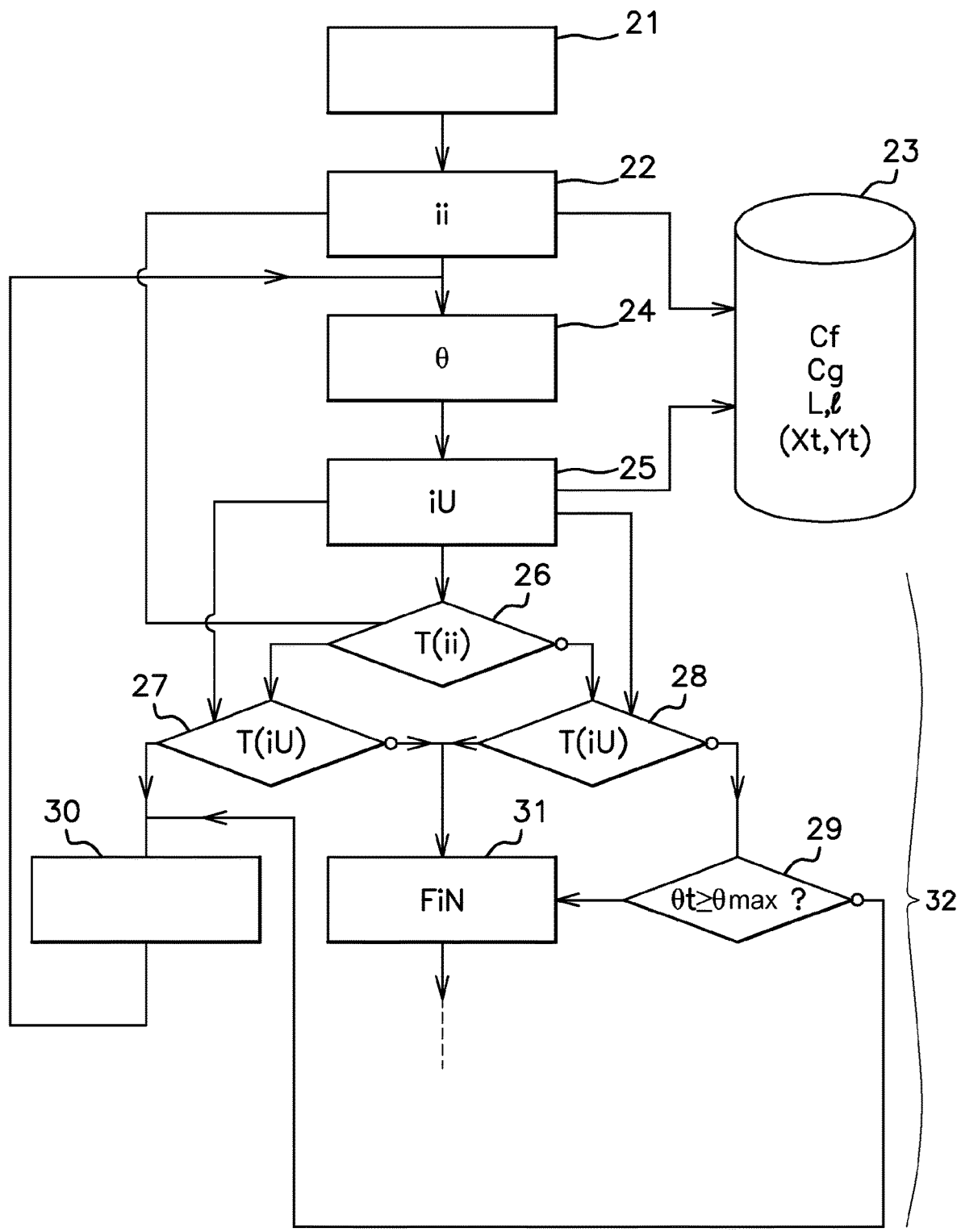
FIG. 18 is a flow chart of the first orientation phase of an orientation method according to one embodiment of the invention.

In FIGS. 17 and 18, the rectangles and the diamonds identify the steps and the tests, which are identified by the reference numerals mentioned hereafter. The tests are show n in accordance with standard ISO 5807.

DETAILED DESCRIPTION

Figure 19:
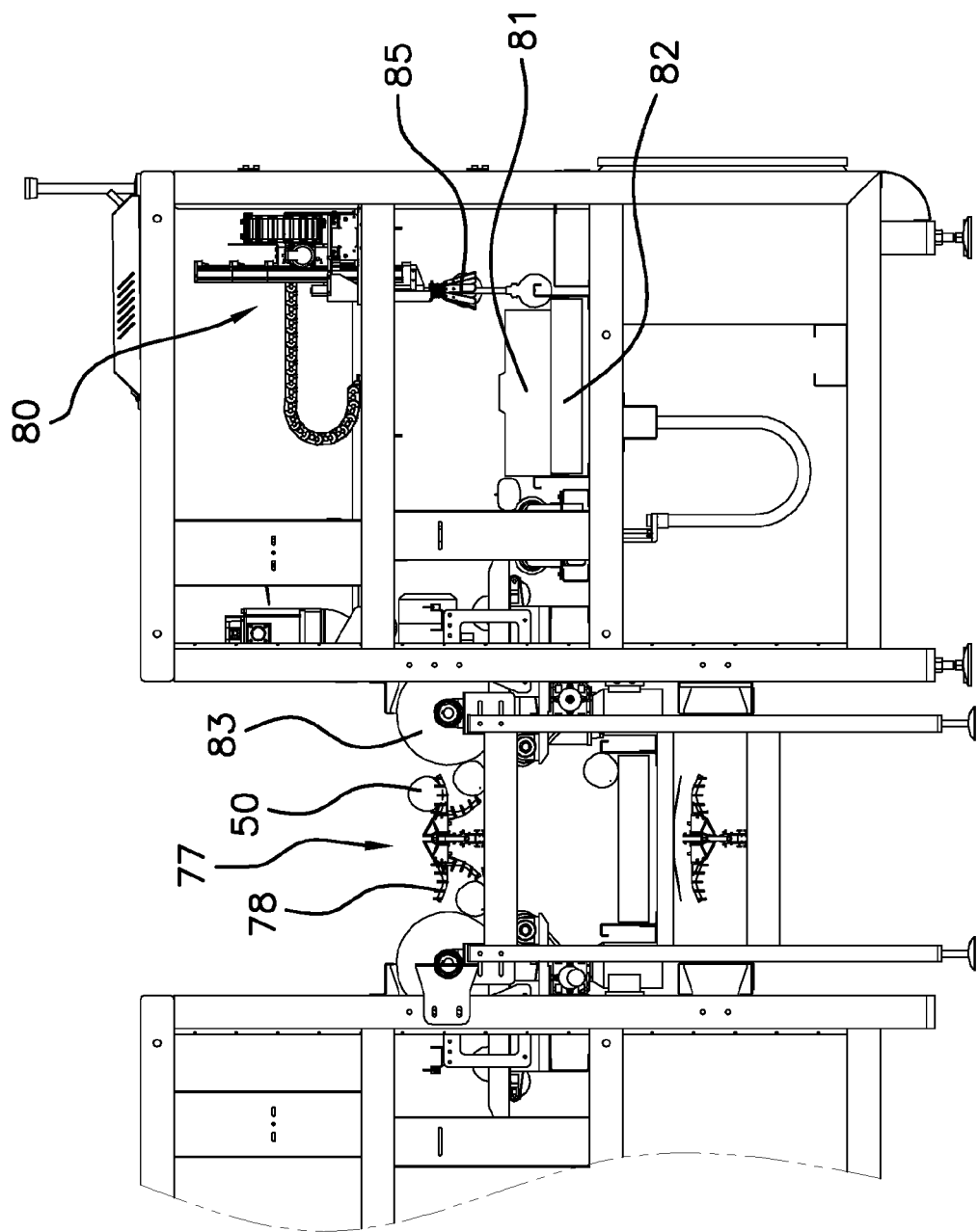
FIG. 19 is an elevation view showing a packaging device according to the invention.
Figure 20:
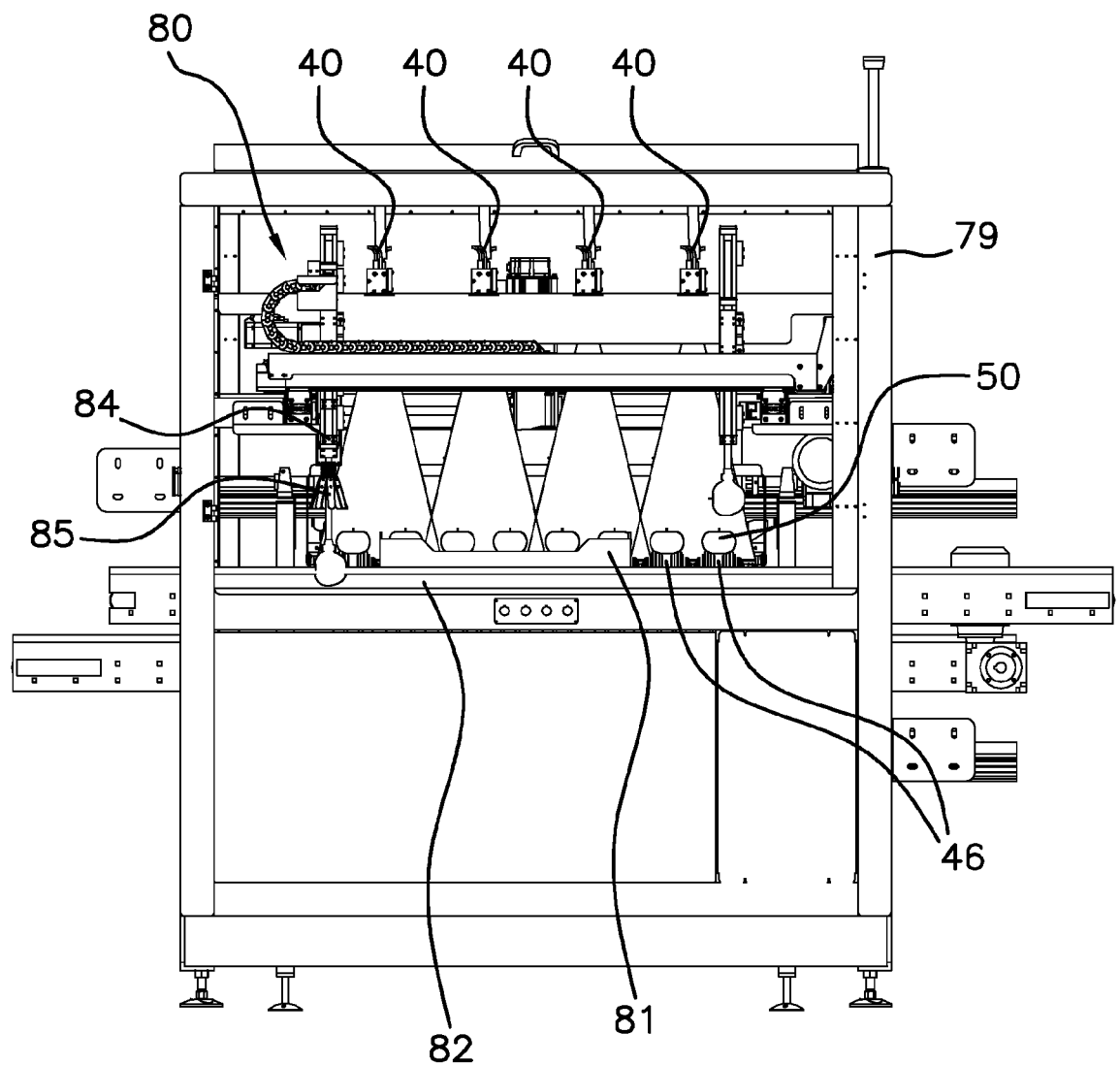
FIG. 20 is a side view of the device of FIG. 19.

In a first loading step 11, an umbilicated fruit is loaded onto a device for orienting an umbilicated fruit according to the invention. This umbilicated fruit can be supplied at the output of a grading unit, as disclosed, for example, in document U.S. Pat. No. 5,626,238 or in document EP 0670276. In this way, the mean grade, i.e. the mean diameter, of the umbilicated fruit is determined. A fruit can be loaded onto an orientation device by any suitable means transferring fruit onto an orientation device of a bank formed by a plurality of orientation devices that are adjoining at the output of the grading unit (FIGS. 19 and 20).

By way of a variation, the orientation dev ice can be integrated into a conveyor comprising a plurality of orientation devices driven in a loop, with this conveyor being synchronously driven with another fruit carrying conveyor (for example, a conveyor of a fruit grading unit) in order to produce an orientation line for the fruit (as disclosed in EP 1183197, for example). In this ease, the loading step 11 is a step involving the orientation device taking over the fruit.

Figure 1:
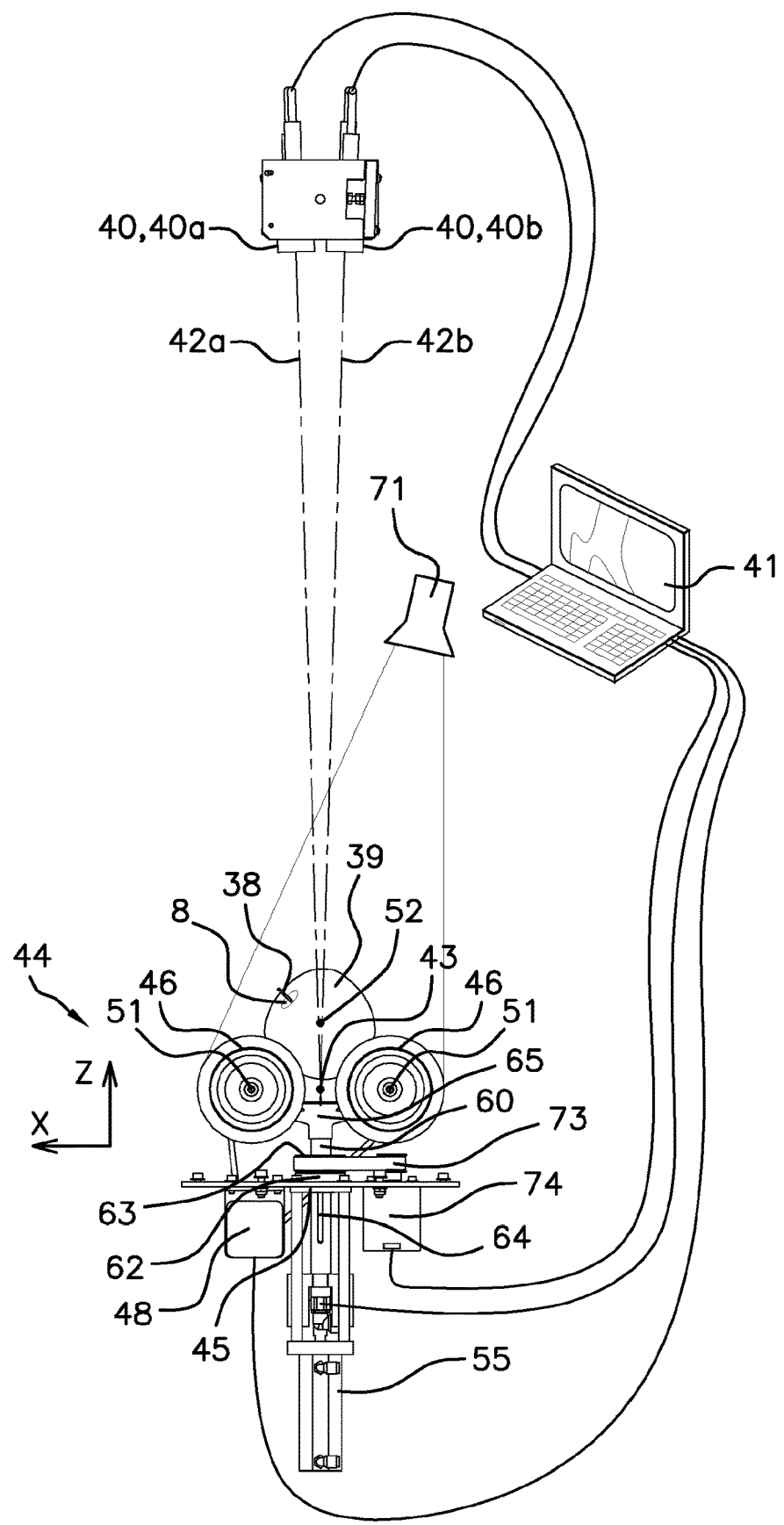
FIG. 1 is a diagram showing an orientation device according to one embodiment of the invention.

Each orientation device according to the invention particularly comprises an optical analysis device comprising at least one camera 40, which is arranged to be able to capture images of an umbilicated fruit loaded on the orientation device, and a computer processing unit 41 receiving the signals delivered by each camera 40 and adapted to be able to analyse the images formed by said camera, and in particular to detect the presence or the lack of presence of an umbilicated fruit on the orientation device. This computer processing unit 41 advantageously is a digital data processing computer unit, with each camera 40 supplying digital data representing images of the fruit. In the example shown in FIG. 1, the orientation device comprises two cameras 40a, 40b, for example, one 40a of which captures images in the visible domain and the other one 40b of which captures images in the infrared domain.

The two cameras 40a, 40b adjoin so that their respective optical image capturing axes 42a, 42b are very close to each other and converge at a point 43 of a support 44 of the orientation device allowing a fruit to be supported and to be set into spinning rotation.

For example, the fruit is illuminated by an infrared light source 71, which is oriented towards the support 44 towards the fruit and the wavelength of which is of the order of 740 nm, and the infrared camera 40b is a camera sensitive to wavelengths between 350 nm and 1,100 nm associated with a high-pass filter having a cut-off wavelength of the order of 695 nm. The camera 40a that is sensitive in the wavelengths of the visible domain is advantageously provided with a band-pass filter, the wavelength band of which is between 390 nm and 690 nm, for example.

If the presence of a fruit on the support 44 of an orientation device is detected by the optical analysis device, the support 44 is controlled by the computer processing unit 41, so as to execute steps of orienting the fruit, as described in further detail hereafter.

The support 44 of an orientation device comprises a horizontal plate 45 supporting two rollers 46 rotationally mounted on shafts 47 supported and rotationally guided relative to the plate 45 on horizontal axes 51 of rotation that are parallel to each other. The two rollers 46 are set into rotation in the same direction of rotation by an electric motor 48 via a belt 49. They are spaced apart from each other by a distance that is adapted to allow them to together support a single fruit 50. The rotation of the rollers 46 thus sets the fruit 50 into spinning rotation about itself on the rollers 46 about a first axis 52 of rotation parallel to the axes 51 of rotation of the rollers 46.

The axes 51 of rotation of the rollers 46 define a horizontal plane, in which an axis X can be defined that is perpendicular to the axes 51 of rotation of the rollers 46, and an axis Y parallel to the axes 51 of rotation of the rollers 46. The vertical direction perpendicular to this horizontal plane and to the axes X and Y defines a vertical axis Z, the axes X, Y, Z define an orthogonal coordinate system shown in the figures.

The support 44 also supports a lifting rod 60 interposed halfway between the two axes 51 of rotation of the rollers 46 and which extends vertically and upwards between the two rollers 46, orthogonal to the axes 51 of rotation of these rollers 46. The lifting rod 60 is guided and set into rotation about its vertical axis 61 relative to the plate 45 of the support 44 through which it passes. To this end, the plate 45 supports a bearing 62 rotationally guiding a wheel 63 having an internal bore passing through a keyway(s) or groove(s) through which the lifting rod 60 passes. The lifting rod 60 has at least one longitudinal slot 64 adapted to be able to slide along at least one keyway or groove of the internal bore of the wheel 63, so that the lifting rod 60 can translationally move on its axis 61 relative to the wheel 63, whilst still being constrained to rotate with this wheel 63 about its axis 61.

The wheel 63 is set into rotation about the axis 61 of the lifting rod 60 in one direction or the other relative to the plate 45 by a belt 73 coupled to an electric motor 74 borne by the plate 45.

The lifting rod 60 is hollow and therefore has an axial through-bore and has a suction pad 65 at its upper end. Its lower end 66 is crimped in a slide 67, so as to be able to be set into translation movement by this slide 67 and to be able to be set into rotation about its axis 61 relative to this slide 67. The slide 67 has a rotary pneumatic connector 68 connected to the lower free end 66 of the lifting rod 60, so as to connect said lower free end 66 to a suction air source (not shown), whilst allowing the lifting rod 60 to rotate about its axis 61, while the connector 68 is fixed relative to the slide 67.

The slide 67 is guided under the plate 45 by four slides 69, fixed under the plate 45, extending vertically downwards to a support plate 70, on which a body 55 of an actuator 53 is fixed, with the activating rod 54 of the actuator vertically passing through the support plate 70 in order to be connected to the slide 67.

Figure 2A:
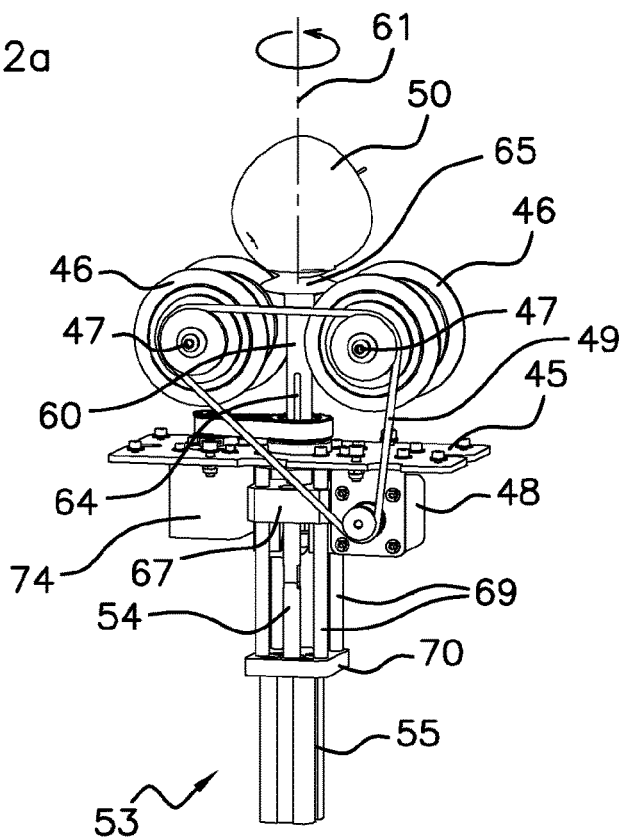
FIG. 2a is a schematic perspective view showing a fruit support of an orientation device according to one embodiment of the invention, with the lifting rod for rotational drive on the second axis of rotation being deployed, the fruit being borne by this lifting rod.
Figure 2B:
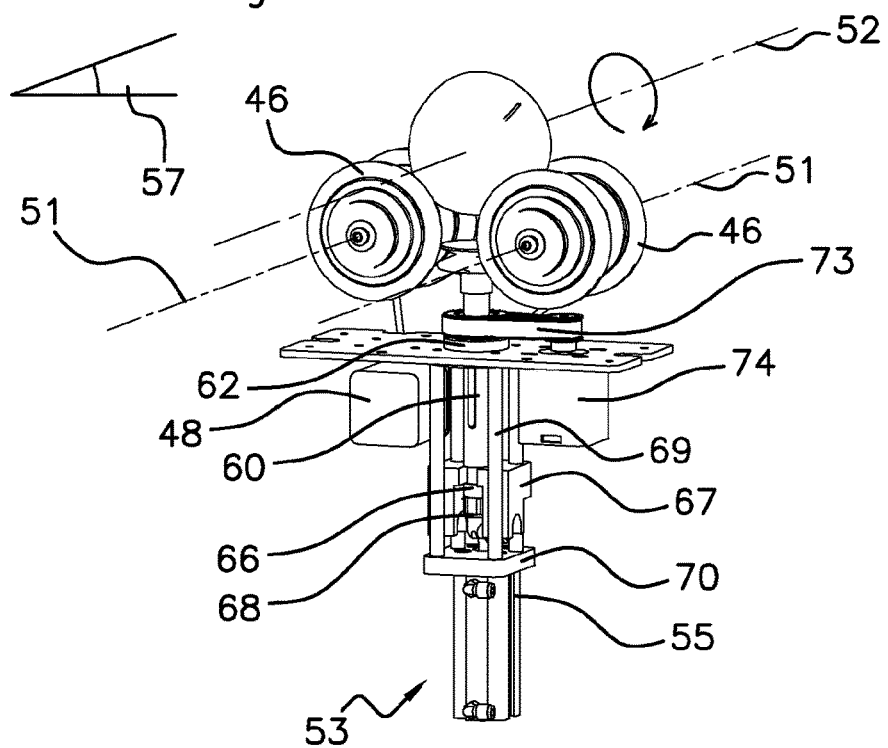
FIG. 2b is a schematic perspective view similar to FIG. 2a, but viewed from the opposite side, with the lifting rod for rotational drive on the second axis of rotation being retracted, the fruit being borne by the rollers of the support.

When the rod 54 for activating the actuator 53 is retracted in the body 55, the slide 67 is in the low position against the support plate 70, the lifting rod 60 is retracted downwards and the suction pad 65 extends between the rollers 46 at a distance from a fruit supported between these rollers 46 (FIG. 2b). The suction pad 65, which is not supplied with suction air, is not in contact with the fruit and does not engage therewith. When the rod 54 for activating the actuator 53 is deployed, the slide 67 is in the high position immediately below the plate 45, the lifting rod 60 is deployed upwards and the suction pad 65 extends upwards above the rollers 46, so as to lift and support a fruit previously supported between the rollers 46. The suction pad 65 being supplied with suction air supports the fruit and, when the electric motor 74 is activated mid the lifting rod 60 is set into rotation about its vertical axis 61, the fruit borne by the suction pad 65 and secured thereto is also set into spinning rotation about this vertical axis 61. The vertical axis 61 of the lifting rod 60 define a second axis 61 of spinning rotation of the fruit orthogonal to the first axis 52 of spinning rotation of the fruit. This second axis 61 of spinning rotation, which is located midway between the axes 51 of rotation of the rollers 46, is at least substantially perpendicular to the first axis 52 of spinning rotation of the fruit. However, it is to be noted that, in this embodiment of the orientation device according to the invention, if the second axis 61 of spinning rotation has, by construction, a fixed position and orientation relative to the rollers 46, this is not the case for the first axis 52 of spinning rotation, the position and the orientation of which are only approximately defined relative to the rollers 46, taking into account the shape and the dimensions of the outer surface of the fruit 50 that runs on the rollers 46. Thus, the second axis 61 of spinning rotation may not strictly intersect with the first axis 52 of spinning rotation, depending on the particular shape and dimensions of the fruit. In the embodiment shown, the first axis 52 of spinning rotation is contained in a horizontal plane and the second axis 61 of rotation is vertical. The vertical translation movements of the lifting rod 60 parallel to the vertical axis Z are controlled by the actuator 53.

The optical image capturing axes 42a, 42b of the cameras 40a, 40b are at least substantially parallel to the vertical axis Z, and thus to the second axis 61 of spinning rotation of the fruit, so that the cameras allow images to be captured of an upper surface 39 of the fruit 50 supported by the rollers 46 or by the lifting rod 60, so that the computer processing unit 41 carries out an optical analysis of this upper surface 39 of the fruit. Initially, during the loading step 11, the lifting rod 60 is in the retracted position, so that when a fruit is loaded onto the support 44, this fruit is supported by the rollers 46.

As soon as a fruit is detected during a step 21 of detecting the fruit on the support 44 by either of the cameras 40a, 40b, a first phase 12 of orienting the fruit is carried out at the command of the computer processing unit 41, so as to place each umbilicus 8, 9 and the umbilical axis 10 in a plane, named first orientation plane 57, that contains said first axis 52 of spinning rotation and is not parallel to the optical image capturing axis 42b, particularly at least substantially perpendicular to this optical image capturing axis 42b. The first orientation plane 57 is perpendicular to the second axis 61 of spinning rotation and to the vertical axis Z, i.e. parallel to the horizontal plane X, Y containing the axes 51 of the rollers 46.

To this end, at least one first image, named initial image, of the fruit is captured during a step 22 of initial optical analysis, so as to determine, and record in a memory 23 of the computer processing unit 41, various dimensional parameters of the fruit and to detect the presence of at least one portion of an umbilicus 8, 9 in this initial image. FIG. 3 schematically shows these various dimensional parameters: the maximum length L of the fruit on the axis X (L=Xmax−Xmin), the maximum width l of the fruit on the axis Y (l=Ymax−Ymin), the position (XCf, YCf) of the geometrical centre Cf of the fruit (for example, XCf is the centre of the segment of length L and YCf is the centre of the segment of length l), the position (XCg, YCg) of the centre Cg of gravity of the fruit (which can be assessed on the basis of the barycentre of the pixels of the initial image), the coordinates (Xt, Xt) of at least one portion of an umbilicus possibly detected in the initial image by the presence of a dark spot T(II), these coordinates (Xt, Yt) corresponding to the centre of the dark spot T(II). These dimensional parameters can be determined on the basis of an initial image captured in the infrared domain by the camera 40*b*.

At least one initial image, named initial infrared image II, is captured using the infrared camera 40*b*, and the presence of at least one portion of an umbilicus in this initial infrared image II is detected in the form of a dark spot T(II), for example, having a grey scale greater than a predetermined grey scale and smaller than the fruit, but larger than a predetermined dimension, this predetermined grey scale and this predetermined dimension can be experimentally defined as a function of the geometrical features of the fruit to be processed, so as to provide reliable detection of the umbilicus in the image. This detection is carried out, for example, using an image processing algorithm comprising a convolution and a convolution kernel.

After this step 22 of initial optical analysis, the computer processing unit 41 commands, during a rotation step 24, the rotation of the rollers 46, so as to set the fruit into spinning rotation about the first axis 52 of spinning rotation. To this end, if a dark spot T(II) corresponding to at least one portion of an umbilicus 8, 9 is detected in the initial infrared image II, the computer processing unit 41 determines the respective positions of the centre Cf of the firm and of the detected dark spot T(II).

The computer processing unit 41 commands the rotation of the rollers 46 in a direction that is determined on the basis of the analysis of an initial two-dimensional image in order to move, in this initial two-dimensional image, the detected umbilicus away from the centre Cf of the fruit, which allows the angular movement amplitude of the umbilicus 8, 9 to be minimised towards the first orientation plane 57. As can be seen in FIGS. 4*a*, 4*b*, with the dark spot T(II) corresponding to the umbilicus 8, 9 being to the right of the centre Cf of the fruit, the rollers 46 are set into rotation in the direction of the arrows shown in said FIGS., so as to set the fruit into spinning rotation about the first axis 52 of spinning rotation in the clockwise direction of FIG. 4*a*. By contrast, in the situation shown in FIGS. 5*a* and 5*b*, with the dark spot T(II) corresponding to the umbilicus 8, 9 being to the left of the centre Cf of the fruit, the rollers 46 are set into rotation in the direction of the arrows shown in said FIGS., so as to set the fruit into spinning rotation about the first axis 52 of spinning rotation in the counter-clockwise direction of FIG. 5*a*.

Upon each rotation step 24, the fruit is set into spinning rotation about the first axis 52 of rotation at an angular amplitude θ between 5° and 45°. More specifically, the fruit is driven at an angular amplitude θ between 10° and 20°, in particular of the order of 15° for apples, with this angular amplitude value θ particularly depending on the optical analysis technique used to detect the umbilicus 8, 9 in the image and on the average relative dimensions of the umbilical depression of each umbilicus of the fruit. The optimal value can be determined experimentally. In particular, it must be low enough to ensure that the fruit is effectively moved (without slippage) and to provide sufficient accuracy of movement, particularly so that the umbilicus is correctly oriented after the rotation if only one portion of this umbilicus is detected in the initial image. It is large enough to optimise the duration of this step and of the entire method.

After having completed this rotation step 24, the computer processing unit 41 commands a new step 25 of optical analysis, named step 25 of subsequent optical analysis, during which at least one infrared image, named subsequent infrared image IU, of the fruit is captured by the infrared camera 40*b* and is on the same optical image capturing axis 42*b* as the initial infrared image II, and this subsequent infrared image is analysed by optical analysis in order to detect the presence of a dark spot T(IU) corresponding to at least one portion of an umbilicus 8, 9 in this subsequent infrared image IU, in the same way as the detection of an umbilicus 8, 9 in the initial infrared image II. At the end of this step 25 of subsequent optical analysis, if an umbilicus 8, 9 is detected in the subsequent infrared image, the coordinates (Xt, Yt) of the centre of the dark spot T(IU) corresponding to this umbilicus are recorded in the bulk memory 23.

After the step 25 of subsequent optical analysis, a step 32 of conditional decision-making is executed by the computer processing unit 41. In this step 32 of conditional decision-making, a first test 26 is executed by the computer processing unit 41 to determine whether the initial infrared image II contains a dark spot T(II) corresponding to at least one portion of an umbilicus 8, 9. If this first test 26 determines that at least one portion of an umbilicus 8, 9 is detected in the initial infrared image II, a second test 27 is subsequently executed by the computer processing unit 41 to determine whether the subsequent infrared image IU also contains a dark spot T(IU) corresponding to at least one portion of an umbilicus 8, 9.

If the second test 27 determines that at least one portion of an umbilicus 8, 9 is detected in the subsequent infrared image IU, the computer processing unit 41 replaces, during the subsequent step 30, the initial infrared image II with the subsequent infrared image IU, and resumes the first orientation phase 12 by repeating the steps of rotation 24, then of subsequent optical analysis 25, then of conditional decision-making 32, by thus considering the preceding subsequent infrared image as a new initial infrared image.

If the second test 27 determines that no umbilical portion 8, 9 has been detected in the subsequent infrared image IU, the first orientation phase 12 is stopped during step 31 and the method is continued, as described hereafter.

If the first test 26 determines that no portion of an umbilicus 8, 9 has been detected in the initial infrared image II, a second test 28 is subsequently executed by the computer processing unit 41 to determine whether the subsequent infrared image IU also contains a dark spot T(IU) corresponding to at least one portion of an umbilicus 8, 9.

If the second test 28 determines that no portion of an umbilicus 8, 9 has been detected in the subsequent infrared image IU, the first orientation phase 12 is stopped during step 31 and the method is continued, as described thereafter.

If the second test 28 determines that no portion of an umbilicus 8, 9 has been detected in the subsequent infrared image IU, a third test 29 is executed to determine; whether the total angular amplitude θt of the rotation of the fruit resulting from the (various) step(s) 24 of rotation carried out during the first orientation phase 12 is or is not greater than or equal to a predetermined angular amplitude, named maximum rotation amplitude θ max, between 180° and 360°, particularly of the order of 270°. If so, the first orientation phase 12 is stopped during step 31 and the method is continued, as described hereafter. If not, the computer processing unit 41 replaces, during the subsequent step 30, the initial infrared image II with the subsequent infrared image IU, and resumes the first orientation phase 12 by repeating the steps of rotation 24, then of subsequent optical analysis 25, then of conditional decision-making 32, by thus considering the preceding subsequent infrared image as a new initial infrared image.

At the end of this first orientation phase 12 with spinning rotation of the fruit about the first axis 52 of rotation, the umbilical axis 10 of the fruit is oriented, at least substantially, in the first orientation plane 57, with a high degree of reliability. The various tests carried out with various fruit with different shapes and different grades have shown that this result is actually achieved more or less systematically, in any case, substantially reliably to be able to contemplate its use on an industrial scale.

After this first orientation phase 12, the method is continued with a second orientation phase 33 with spinning rotation of the fruit about the second axis 61 of rotation, which is perpendicular to the first orientation plane 57. To this end, the computer processing unit 41 identifies, during the step 13, the last infrared image DI that was captured and in which at least one portion of an umbilicus 8, 9 has been detected by optical analysis. This last infrared image DI containing at least one portion of an umbilicus can be an initial infrared image or a subsequent infrared image.

During the subsequent step 14, the computer processing unit 41 determines the position of the centre Cf of the fruit in this last infrared image DI and computes the value of an angle, named azimuth γ, formed between the first axis 52 of rotation and the umbilical axis 10 determined during this step 14 as being the axis passing through the centre of the dark spot corresponding to the detected umbilicus 8, 9 and the centre Cf of the fruit.

During the subsequent step 15, the computer processing unit 41 commands tire spinning rotation of the fruit about the second axis 61 of rotation at an angular amplitude that is determined by the computed azimuth value γ, so as to orient the umbilical axis 10 at least substantially parallel to the first axis 52 of rotation.

Figure 6A:
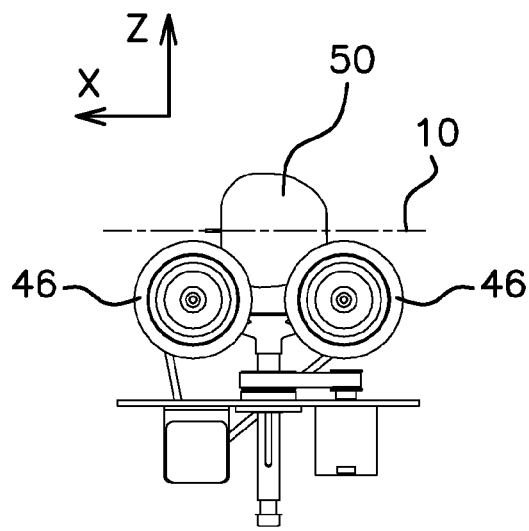
FIGS. 6a and 6b are schematic elevation and top views, respectively, of a fruit support of an orientation device showing a first example of the orientation of a fruit at the end of a first orientation phase of an orientation method according to one embodiment of the invention.
Figure 7A:
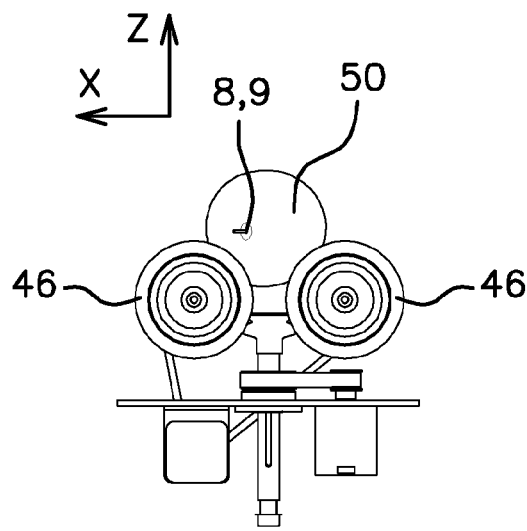
FIGS. 7a and 7b are schematic elevation and top views, respectively, of a fruit support of an orientation device showing a second example of the orientation of a fruit at the end of a first orientation phase of an orientation method according to one embodiment of the invention.
Figure 6B:
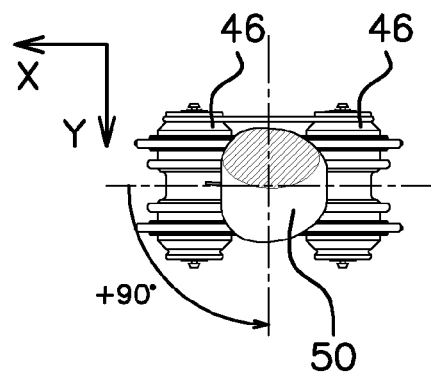
Figure 7B:
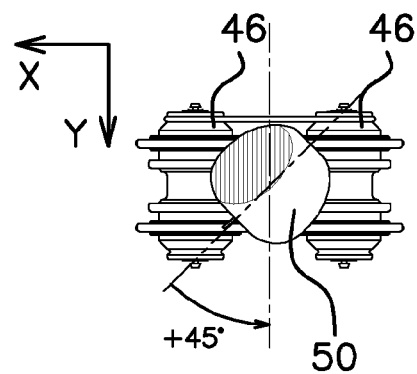

In the example shown in FIGS. 6a and 6b, the umbilical axis 10 is perpendicular to the first axis 52 of rotation at the end of the first rotation phase 12. The azimuth γ of the umbilical axis 10 therefore is 90°. During the step 15 of rotation about the second axis 61 of rotation, the fruit therefore is set into spinning rotation by the lifting rod 60 at an angular amplitude of 90° about the second axis 61 of rotation. In the example shown in FIGS. 7a and 7b, the umbilical axis 10 forms an angle of the order of 45° with the first axis 52 of rotation at the end of the first rotation phase 12. The azimuth γ of the umbilical axis 10 therefore is 45°. During the step 15 of rotation about the second axis 61 of rotation, the fruit therefore is set into spinning rotation by the lifting rod 60 at an angular amplitude of 45° about the second axis of rotation 61.

Figure 8:
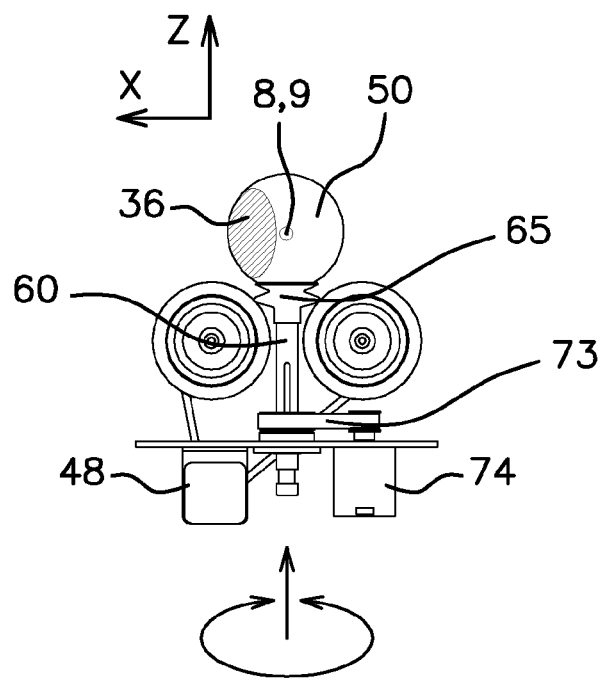
FIG. 8 is a schematic elevation view of a fruit support of an orientation dev ice during a second orientation phase of an orientation method according to one embodiment of the invention.
Figure 9:
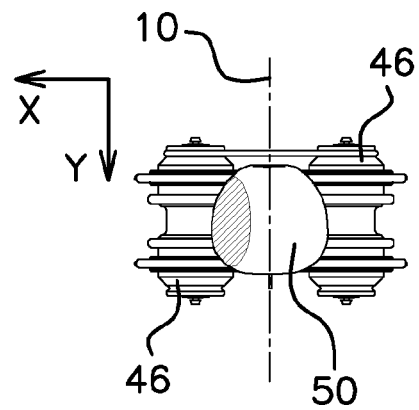
FIG. 9 is a schematic top view of a fruit support of an orientation device at the end of a second orientation phase of an orientation method according to one embodiment of the invention.
Figure 10:
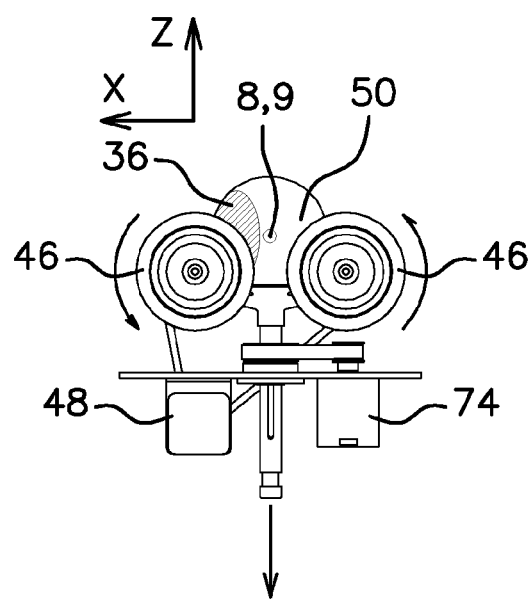
FIG. 10 is a schematic elevation view of a fruit support of an orientation device during a third orientation phase of an orientation method according to one embodiment of the invention.
Figure 11:
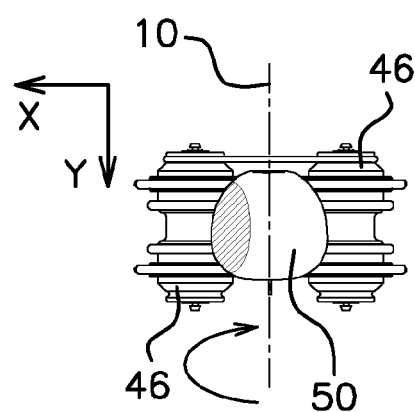
FIG. 11 is a schematic top view of FIG. 10.

At the end of the second orientation phase 33 by rotation about the second axis 61 of rotation, the umbilical axis 10 is in the first orientation plane 57 and is parallel to the first axis 52 of rotation, i.e. to the axes 51 of rotation of the rollers 46, as shown in FIGS. 8 and 9.

Figure 12:
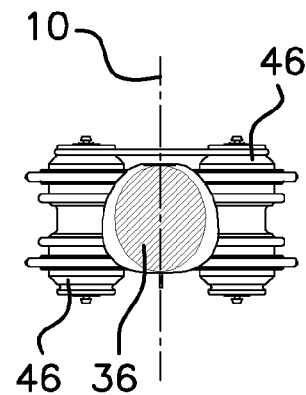
FIG. 12 is a schematic top view of a fruit support of an orientation device at the end of the third orientation phase of an orientation method according to one embodiment of the invention.
Figure 13:
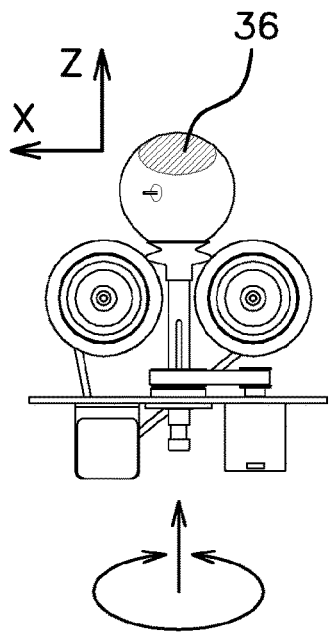
FIG. 13 is a schematic elevation view of a fruit support of an orientation device during a fourth orientation phase of an orientation method according to one embodiment of the invention.

After the second orientation phase 33, the computer processing unit 41 executes a third orientation phase 34 allowing the most colourful portion 36 of the fruit, i.e. having a maximum amount of colour, to be placed upwards. To this end, during the step 16, the fruit is continuously set into spinning rotation by the rollers 46 about the first axis 52 of rotation, at an angular amplitude at least equal to 360°. At the same time, an optical analysis of the fruit is earned out by the camera 40a in the visible domain and the images of the various surface portions of the fruit are recorded during the rotation about the first axis 52 of rotation. In this way, the computer processing unit 41 determines the image thus captured that corresponds to the most colourful portion 36 of the fruit as well as its angular position about the first axis 52 of rotation. During the subsequent step 17, the computer processing unit 41 controls the rotation of the rollers 46, such that the most colourful portion 36 of the fruit is oriented upwards, i.e. towards the camera 40a, as shown in FIG. 12.

When the fruit is a stalked fruit, such as an apple, the computer processing unit 41 executes a fourth orientation phase 37 allowing the stalk 38 of the fruit to be oriented in a predetermined direction and in a predetermined angular position relative to the first axis 52 of rotation, so that all the fruit thus oriented all show the stalk 38 oriented in the same direction.

Figure 16:
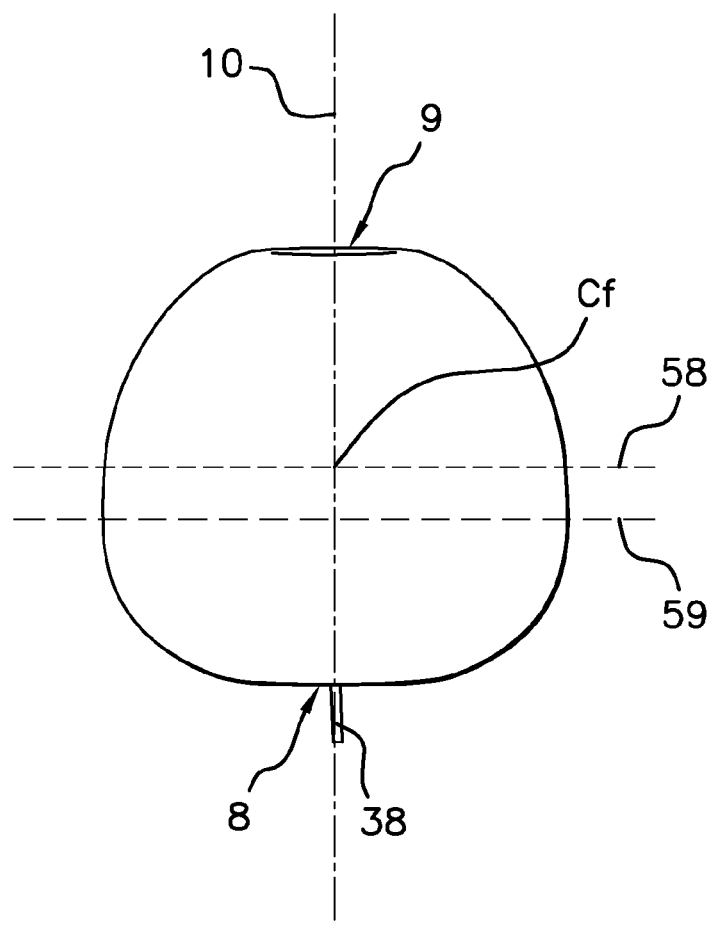
FIG. 16 is an example of an image of a fruit allowing morphological analysis of said fruit.

The computer processing unit 41 firstly executes a step 18 of morphological optical analysis allowing the position of the stalk 38 of the fruit to be detected. To this end, the computer processing unit 41 analyses an image captured after the second orientation phase 33 in the visible domain by the camera 40a, as shown in FIG. 16 in the example of an apple, in order to determine:

the position of a plane, named equatorial plane 58, perpendicular to the umbilical axis 10 and having the largest diameter of the fruit corresponding to the largest value of the length L on the axis X in this image; and the position of a plane, named central plane 59, perpendicular to the umbilical axis 10 and passing through the centre Cf of the fruit.

Indeed, in the case of an apple, the equatorial plane 58 is closer to the stalk 38 than the central plane 59. Of course, other morphological analysis criteria can be used, as a function of the general morphology of the fruit, to detect the position of the stalk.

Figure 14A:
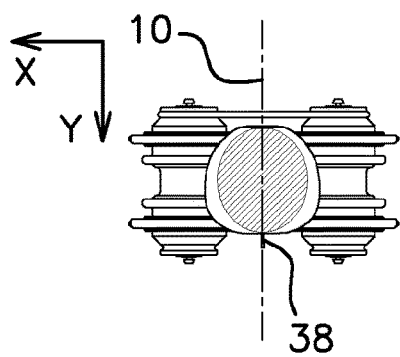
FIGS. 14a and 14b are schematic top views of a fruit support of an orientation device at the start and, respectively, at the end of a first example of the fourth orientation phase of an orientation method according to one embodiment of the invention.
Figure 15A:
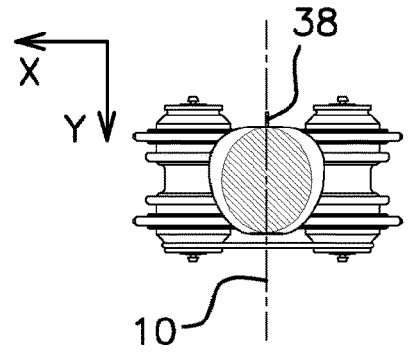
FIGS. 15a and 15b are schematic top views of a fruit support of an orientation device at the start and, respectively, at the end of a second example of the fourth orientation phase of an orientation method according to one embodiment of the invention.
Figure 14B:
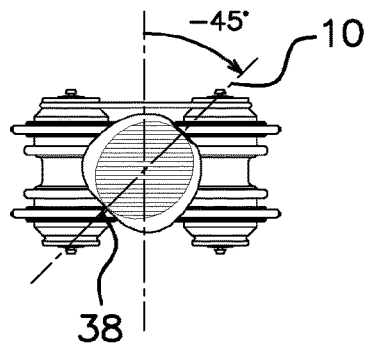
Figure 15B:
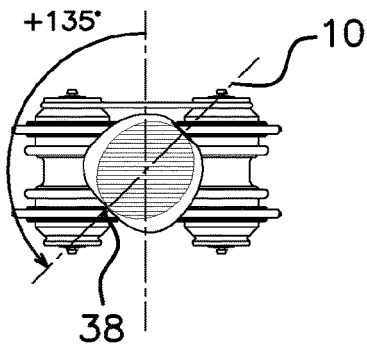

This morphological optical analysis therefore allows the position of the stalk 38 on the umbilical axis 10 to be determined. During the subsequent step 19, the computer processing unit 41 sets the fruit into spinning rotation about the second axis 61 of rotation in a predetermined direction and at a predetermined angular amplitude for placing the stalk 38 in a predetermined angular position relative to the first axis 52 of rotation, for example, at 45°, as shown in FIGS. 14b and 15b. Thus, according to the position of the stalk 38 determined during the step 18 of morphological optical analysis, the fruit is set into spinning rotation either by 45° in the clockwise direction (the example of FIGS. 14a and 14b) or by 135° in the counter-clockwise direction (the example of FIGS. 15a and 15b).

At the end of this fourth orientation phase 37, the fruit has a predetermined orientation with the umbilical axis 10 in the first orientation plane 57, inclined at 45° relative to the first axis 52 of rotation, with the stalk 38 always located on the same side and the coloured portion 36 facing upwards.

The packaging device according to the invention shown in FIGS. 19 and 20 comprises a frame 79 supporting a plurality of orientation devices juxtaposed on each side of a conveyor 77 with tilting hands 78 allowing the fruit 50 to be unloaded on either side of the conveyor 77, selectively on the rollers 46 of one of the supports 44 of these orientation devices. A rotary brush 83 breaks the fall of the fruit. The packaging device has, in the example shown, two packaging stations, one on each side of the conveyor 77, and symmetrical with each other relative to a vertical longitudinal central plane of the conveyor 77, with each packaging station particularly comprising a handling robot 80 and a conveyor 82 carrying empty cellular packages 81 under the handling robot 80.

In FIG. 19, only one of the packaging stations is shown. This packaging station comprises, in the example, eight supports 44 for eight orientation devices juxtaposed along the conveyor 77. In the example shown, the handling robot 80 comprises a vertical arm 84 supporting a hand 85 for gripping a fruit 50 at its lower free end, with this arm 84 supporting a vertical actuator allowing the gripping hand 85 to be moved vertically and an actuator for controlling its activation, and these being supported by a gantry that is adapted to be able to move the arm 84 in horizontal translation movements relative to the frame 79 in two horizontal orthogonal directions. Each camera 40 captures images of the fruit on two juxtaposed orientation devices and each infrared light source 71 illuminates at least two juxtaposed orientation devices.

During the packaging step 20, the fruit 50 therefore can be grasped by the handling robot 80 in order to be able to be placed in a cellular package 81 (crates, trays, etc.) in a predetermined optimal orientation. To this end, the computer processing unit 41 sends, to a unit for controlling the handling robot, the coordinates of the fruit, and those of the position of a cell intended to receive this fruit in a package 81 to be filled that is placed by a conveyor 82 under the handling robot 80. The unit for controlling the robot 80 generates the optimal trajectory to be followed and controls the robot 80 in order to move the fruit. Once the fruit is deposited into the cell, the robot control unit confirms to the computer processing unit 41 that the movement of this fruit in the package 81 has been completed.

An orientation method according to the invention is implemented by the computer programming unit 41, which is programmed to this end by a computer program according to the invention to execute the aforementioned technical functions. To this end, any programming technology and/or computer programming language can be contemplated (for example, C, C++, C#, etc.). Similarly, the unit for controlling the handling robot can be formed by any programmable logic controller.

The invention can be the subject of numerous variations relative to the embodiment that is shown in the FIGS. and is described above. The optical analysis device can comprise cameras 40*a*, 40*b* capable of capturing images of various features, particularly selected from shots in visible light, shots in filtered visible light, shots in the infrared domain and shots in the ultraviolet domain. The invention is applicable to any umbilicated fruit. Furthermore, the images captured by the cameras for the optical analysis can be photographs or videos, the optical analysis carried out by the computer processing unit 41 can be carried out not only on photographs, but also on videos or parts of videos. Other devices and mechanisms for spinning rotation, at least on the two axes 52, 61 that are orthogonal to each other, can be provided instead of the rollers 46 and the lifting rod 60. Furthermore, suitable light sources can also be provided to illuminate the fruit in order to improve the quality of the captured images and the accuracy of the optical analysis, particularly a visible light source and an infrared light source. The various steps of a method according to the invention can be the subject of numerous variations, and intermediate steps can be provided between the aforementioned successive steps, as long as these intermediate steps do not hinder the operation of the method according to the invention, i.e. the execution of each step of conditional decision-making and/or the suitable orientation of the fruit.

The invention particularly allows robotised automatic packaging of fruit to be provided in cellular packages, particularly at the end of a fruit grading line, with all the fruit being oriented in the same way, with the most colourful face towards the top, with each umbilicus and each possible stalk being oriented in the same direction. However, it is also applicable to other applications in which the same problems arise.

The invention claimed is:

1. A method for orienting an umbilicated fruit, comprising the steps of:
   during a first orientation phase the fruit is supported and set into spinning rotation about a first axis of rotation;
   during a second subsequent orientation phase the fruit is supported and set into spinning rotation about a second axis of rotation orthogonal to the first axis of rotation;
   an optical analysis of an upper surface of the fruit is carried out at least during at least part of the first orientation phase using at least one camera, disposed above the fruit, capturing images of said upper surface of the fruit, said images being transmitted to an image processing unit adapted to analyse said images and to produce optical analysis results depending on the orientation of the fruit;
   the rotation of the fruit about each of the two axes of rotation is controlled as a function at least of said optical analysis results of the fruit;
characterised in that:
   the first orientation phase comprises the following steps:
   an initial optical analysis step, during which:
   at least one image, named initial image, of the fruit is captured on an optical image capturing axis not parallel to the first axis of rotation;
   each initial image is analysed by optical analysis, with the presence of at least one portion of an umbilicus being detected in each initial image;
   then a rotation step, during which the fruit is set into spinning rotation about the first axis of rotation at an angular amplitude between 5° and 45°;
   then a subsequent optical analysis step, during which:
   at least one image, named subsequent image, of the fruit is captured on the same optical image capturing axis as the initial image;
   each subsequent image is analysed by optical analysis, with the presence of at least one portion of an umbilicus being detected in each subsequent image;
   the processing unit executes a step of conditional decision-making, according to which, when a first condition is met by the optical analysis results of each initial image and of each subsequent image, the first orientation phase is stopped and the method is continued, said first condition being met when at least one portion of an umbilicus is detected in at least one initial image and is no longer detected in each subsequent image.

2. The method according to claim 1, wherein, when said first condition is not met, the steps of rotation and of subsequent optical analysis of the first orientation phase are repeated, then the step of conditional decision-making is repeated by the processing unit by considering the subsequent image, captured before repeating the steps of rotation and of subsequent optical analysis, as an initial image.

3. The method according to claim 2, wherein, according to the step of conditional decision-making:
   when at least one portion of an umbilicus is detected in at least one initial image and in at least one subsequent image, the steps of rotation and of subsequent optical analysis of the first orientation phase are repeated;

when at least one portion of an umbilicus is not detected either in each initial image or in each subsequent image, the steps of rotation and of subsequent optical analysis of the first orientation phase are repeated, as long as the total angular amplitude of the rotation of the fruit resulting from the various steps of rotation carried out during the first orientation phase is below a predetermined angular amplitude, named maximum rotation amplitude, between 180° and 360°, particularly of the order of 270°;

when at least one portion of an umbilicus is not detected either in each initial image or in each subsequent image, the steps of rotation and of subsequent optical analysis of the first orientation phase are repeated, and if the total angular amplitude of the rotation of the fruit resulting from the various steps of rotation previously carried out during the first orientation phase is greater than or equal to said maximum rotation amplitude, the first orientation phase is stopped and the method is continued;

when at least one portion of an umbilicus is not detected in each initial image but is detected in at least one subsequent image, the steps of rotation and of subsequent optical analysis of the first orientation phase are repeated, then the step of conditional decision-making is repeated by the processing unit by considering the subsequent image, captured before repeating the steps of rotation and of subsequent optical analysis, as an initial image.

4. The method according to claim 1, wherein said optical image capturing axis is at least substantially orthogonal to the first axis of rotation.

5. The method according to claim 1, wherein the first axis of rotation is contained in a horizontal plane and the second axis of rotation is vertical.

6. The method according to claim 1, wherein said step of initial optical analysis comprises the detection of a centre of the fruit in at least one initial image, and, when at least one portion of an umbilicus is detected in at least one initial image, during the subsequent rotation step the fruit is set into rotation in a direction that is determined by the respective detected positions of the centre of the fruit and of the umbilicus, and is selected to minimise the angular movement amplitude of the umbilicus towards a plane, named first orientation plane, containing the first axis of rotation and not parallel to the optical image capturing axis.

7. The method according to claim 1, wherein, during each optical analysis step, at least one image, named infrared image, is captured using at least one infrared camera, and the presence of at least one portion of an umbilicus is detected in each infrared image in the form of a spot having a grey scale that is higher than a predetermined grey scale and is smaller than that of the fruit but is larger than a predetermined dimension.

8. The method according to claim 1, wherein the second axis of rotation is perpendicular to a plane, named first orientation plane, containing the first axis of rotation and not parallel to the optical image capturing axis.

9. The method according to claim 1, wherein, at the end of the first orientation phase, the processing unit:

identifies the last captured image, in which at least one portion of an umbilicus is detected by optical analysis, determines the position of a centre of the fruit in this last image, and computes the value of an angle, named azimuth, formed between the first axis of rotation and an axis, named umbilical axis, passing through the umbilicus and the centre of the detected fruit;

then commands a rotation of the fruit about the second axis of rotation during the second orientation phase at an angular amplitude that is determined by the computed azimuth value, so as to orient the umbilical axis at a predetermined orientation relative to the first axis of rotation.

10. The method according to claim 1, wherein said method comprises, after the second orientation phase, a subsequent orientation phase, during which:

the fruit is supported and set into rotation over an angular rotation amplitude of at least 360° about the first axis of rotation;

an optical analysis of an upper surface of the fruit is carried out to detect a portion of said upper surface, named most colourful portion, having a maximum amount of colour;

the rotation of the fruit is interrupted so as to place said most colourful portion on top.

11. The method according to claim 1 for orienting a stalked fruit, wherein said method comprises, after the second orientation phase, a step of morphological optical analysis adapted to allow the position of a stalk of the fruit to be detected.

12. The method according to claim 11, wherein said method comprises, after the step of morphological optical analysis, a subsequent step of rotation, during which the fruit is set into rotation about the second axis of rotation at a determined angular amplitude for placing the stalk in a predetermined angular position relative to the first axis of rotation.

13. A device for orienting an umbilicated fruit, comprising:

a first fruit support adapted to support a fruit and to set it into spinning rotation about a first axis of rotation;

a second fruit support adapted to support a fruit and to set it into spinning rotation about a second axis of rotation orthogonal to the first axis of rotation;

a device for optically analysing an upper surface of the fruit, comprising at least one camera disposed above the fruit in order to be able to capture images of said upper surface of the fruit;

a programmable processing unit adapted to:

analyse the images and to produce optical analysis results dependent on the orientation of the fruit;

control the rotation of the fruit about each of the two axes of rotation as a function at least of said optical analysis results of the fruit;

characterised in that said programmable processing unit is programmed to implement an orientation method according to claim 1.

14. The device for packaging umbilicated fruit, comprising devices for orienting fruit and at least one fruit handling robot that is adapted to place each fruit in a cell of a cellular package at a predetermined orientation, wherein said device comprises at least one orientation device according to claim 13.

15. The method for packaging umbilicated fruit in cellular packages, wherein each fruit is placed in a packaging cell at a predetermined orientation, wherein said method comprises a method for orienting each fruit according to claim 1.

16. A non-transitory computer program comprising computer program code instructions, wherein said computer program comprises programming means that can be read by a programmable processing unit and that are adapted to, once executed by said programmable processing unit, execute a packaging method according to claim 15 with said programmable processing unit and with a device for orienting each fruit that is adapted to support and set each fruit into spinning rotation about said first axis of rotation and about said second axis of rotation.

17. A non-transitory computer program comprising computer program code instructions, wherein said computer program comprises programming means that can be read by a programmable processing unit and that are adapted to, once executed by said programmable processing unit, execute an orientation method according to claim 1 with said programmable processing unit and with a device for orienting each fruit that is adapted to support and set each fruit into spinning rotation about said first axis of rotation and about said second axis of rotation.

\* \* \* \* \*